(12) United States Patent
Kimura et al.

(10) Patent No.: US 10,407,362 B2
(45) Date of Patent: Sep. 10, 2019

(54) DIENE PRODUCTION METHOD

(71) Applicant: JXTG NIPPON OIL & ENERGY CORPORATION, Tokyo (JP)

(72) Inventors: Nobuhiro Kimura, Tokyo (JP); Junji Wakabayashi, Tokyo (JP); Sosuke Higuchi, Tokyo (JP)

(73) Assignee: JXTG NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 15/557,678

(22) PCT Filed: Feb. 16, 2016

(86) PCT No.: PCT/JP2016/054439
§ 371 (c)(1),
(2) Date: Sep. 12, 2017

(87) PCT Pub. No.: WO2016/152324
PCT Pub. Date: Sep. 29, 2016

(65) Prior Publication Data
US 2018/0050970 A1   Feb. 22, 2018

(30) Foreign Application Priority Data

Mar. 20, 2015  (JP) ................... 2015-058331
May 29, 2015  (JP) ................... 2015-110059

(51) Int. Cl.
| | | |
|---|---|---|
| C07C 5/25 | (2006.01) | |
| B01J 23/68 | (2006.01) | |
| B01J 29/12 | (2006.01) | |
| B01J 29/14 | (2006.01) | |
| C07B 61/00 | (2006.01) | |
| C07C 11/08 | (2006.01) | |
| C07C 11/16 | (2006.01) | |
| B01J 35/00 | (2006.01) | |
| B01J 23/31 | (2006.01) | |
| B01J 23/887 | (2006.01) | |
| C07C 5/48 | (2006.01) | |
| C07C 7/04 | (2006.01) | |

(52) U.S. Cl.
CPC ............... *C07C 5/25* (2013.01); *B01J 23/31* (2013.01); *B01J 23/681* (2013.01); *B01J 23/686* (2013.01); *B01J 23/8872* (2013.01); *B01J 29/123* (2013.01); *B01J 29/143* (2013.01); *B01J 35/0006* (2013.01); *C07B 61/00* (2013.01); *C07C 5/2556* (2013.01); *C07C 5/48* (2013.01); *C07C 7/04* (2013.01); *C07C 11/08* (2013.01); *C07C 11/16* (2013.01); *B01J 2523/00* (2013.01); *C07C 2521/04* (2013.01); *C07C 2521/08* (2013.01); *C07C 2523/04* (2013.01); *C07C 2523/28* (2013.01); *C07C 2523/31* (2013.01); *C07C 2523/44* (2013.01); *C07C 2523/745* (2013.01); *C07C 2523/75* (2013.01); *C07C 2523/755* (2013.01); *C07C 2523/887* (2013.01); *C07C 2529/12* (2013.01); *C07C 2529/14* (2013.01)

(58) Field of Classification Search
CPC .. C07C 5/25; C07C 11/08; C07C 11/16; B01J 23/681; B01J 23/686; B01J 29/123; B01J 29/143; C07B 61/00
See application file for complete search history.

(56) References Cited

U.S. PATENT DOCUMENTS

| | | | | |
|---|---|---|---|---|
| 3,475,511 A | * | 10/1969 | Manning ................ | B01J 29/061 585/324 |
| 3,479,415 A | * | 11/1969 | Shull ..................... | C07C 5/2506 502/11 |
| 3,911,039 A | * | 10/1975 | Grasselli ............... | B01J 23/8876 502/306 |
| 2005/0080309 A1 | * | 4/2005 | Cano ..................... | C07C 5/2506 585/664 |
| 2011/0040134 A1 | * | 2/2011 | Arnold .................. | C07C 5/2506 585/315 |
| 2016/0318829 A1 | * | 11/2016 | Gaertner ............... | C07C 5/2512 |

FOREIGN PATENT DOCUMENTS

| | | | | |
|---|---|---|---|---|
| CA | 1222529 A1 | * | 6/1987 | |
| DE | 102013226370 A1 | * | 6/2015 | .......... C07C 5/2512 |
| EP | 0129899 A2 | * | 1/1985 | .......... C07C 5/2518 |
| JP | S57-112336 A | | 7/1982 | |

(Continued)

OTHER PUBLICATIONS

Michael E. Gisbon et al., "Oxidation of Dehydrogenation of Butenes over Magenesium Ferrite—Kinetic and Mechanistic Studies", Journal of Catalysis, 1976 (41), p. 420-p. 430.
Yu. M. Bakshi et al., "Catalytic Properties of System SnO2:Sb2O4 in the Oxidative Dehydrogenation of n-Butenes to Butadiene", Petroleum Chemistry U.S.S.R, 1967 (4), p. 177-p. 185.
W. J. Linn et al., "Oxidation of 1-Butene over Bismuth Molybdates and Bismuth Iron Molybdate", Journal of Catalysis, 1976 (41), p. 134-p. 139.
"Handbook of Heterogeneous Catalysis", 1997, p. 2302.
Carmela V. Hidalgo et al., "Measurement of the Acidity of Various Zeolites by Temperature-Programmed Desorption of Ammonia", Journal of Catalysis, 1984 (85), p. 362-p. 369.
International Search Report from Patent Application No. PCT/JP2016/054439 dated May 10, 2016.

(Continued)

*Primary Examiner* — Brian A McCaig
*Assistant Examiner* — Jason Y Chong
(74) *Attorney, Agent, or Firm* — Greenblum & Bernstein, P.L.C.

(57) ABSTRACT

A method for producing diene comprises a step 1 of obtaining a straight chain internal olefin by removing a branched olefin from a raw material including at least the branched olefin and a straight chain olefin; and a step 2 of producing diene from the internal olefin by oxidative dehydrogenation using a first catalyst and a second catalyst, and the first catalyst has a complex oxide including bismuth, molybdenum and oxygen, and the second catalyst includes at least one selected from the group consisting of silica and alumina.

12 Claims, No Drawings

(56) References Cited

FOREIGN PATENT DOCUMENTS

| | | |
|---|---|---|
| JP | S57-140730 A | 7/1982 |
| JP | S59-062532 A | 4/1984 |
| JP | S59-164730 A | 9/1984 |
| JP | S60-001139 A | 1/1985 |
| JP | S60-092224 A | 5/1985 |
| JP | 2003-220335 A | 8/2003 |

OTHER PUBLICATIONS

International Preliminary Report on Patentability from Patent Application No. PCT/JP2016/054439 dated Sep. 26, 2017.
Written Opinion of the International Searching Authority from Patent Application No. PCT/JP2016/054439 dated Oct. 5, 2016.

* cited by examiner

US 10,407,362 B2

DIENE PRODUCTION METHOD

TECHNICAL FIELD

The present invention relates to a method for producing diene.

BACKGROUND ART

Dienes such as butadiene are extremely useful as basic raw materials for use in petrochemical industry.

A diene can be obtained by oxidative dehydrogenation of a monoolefin using a dehydrogenation catalyst. Examples of the monoolefin include propylene, 1-butene and 2-butene.

In the oxidative dehydrogenation of a monoolefin, a metal oxide is conventionally used as the dehydrogenation catalyst. As the metal oxide (the dehydrogenation catalyst), for example, a ferrite-based catalyst (see Non Patent Literature mentioned below), a tin-based catalyst (see Non Patent Literature 2 mentioned below) and a bismuth molybdate-based catalyst (see Patent Literatures 1 to 3 and Non Patent Literatures 3 and 4 mentioned below) are known.

CITATION LIST

Patent Literature

Patent Literature 1: Japanese Unexamined Patent Publication No. S57-140730
Patent Literature 2: Japanese Unexamined Patent Publication No. 560-1139
Patent Literature 3: Japanese Unexamined Patent Publication No. 2003-220335

Non Patent Literature

Non Patent Literature 1: J. Catal., 1976, volume 41, 420
Non Patent Literature 2: Petroleum Chemistry U. S. S. R., 1967, 7, 177
Non Patent Literature 3: J. Catal., 1976, 41, 134
Non Patent Literature 4: Handbook of Heterogeneous Catalysis, 1997, 5, 2302

SUMMARY OF INVENTION

Technical Problem

As a raw material for use in production of a diene, a raw material including a branched olefin and a straight chain olefin is known. When the raw material including a branched olefin and a straight chain olefin is subjected to oxidative dehydrogenation using a conventional dehydrogenation catalyst (a metal oxide), however, it is difficult to produce a diene in a sufficient yield.

The present invention was accomplished in consideration of the above-described problem, and an object is to provide a method for producing diene in which diene can be produced in a high yield by using a raw material including a branched olefin and a straight chain olefin.

Solution to Problem

The method for producing diene according to one aspect of the present invention comprises: a step 1 of obtaining a straight chain internal olefin by removing a branched olefin from a raw material including at least the branched olefin and a straight chain olefin; and a step 2 of producing diene from the internal olefin by oxidative dehydrogenation using a first catalyst and a second catalyst, and the first catalyst has a complex oxide including bismuth, molybdenum and oxygen, and the second catalyst includes at least one selected from the group consisting of silica and alumina.

At least a part of the straight chain olefin may be a terminal olefin, and in the step 1, reactive distillation may be performed to remove the branched olefin from the raw material and to isomerize the terminal olefin to the internal olefin.

The second catalyst may have a support and an element supported on the support, the support may include at least one selected from the group consisting of silica and alumina, and the element supported on the support may be at least one selected from the group consisting of Group 10 elements of the periodic table and Group 11 elements of the periodic table, and lanthanoids.

Ni may be used as the Group 10 element of the periodic table, Cu, Ag or Au may be used as the Group 11 element of the periodic table, and La may be used as the lanthanoid.

Ag may be supported on the support as the Group 11 element of the periodic table.

The second catalyst may include silica and alumina, and a total acid amount of the second catalyst measured by ammonia temperature programmed desorption may be 0.11 mmol/g or less.

The second catalyst may include silica and alumina, and the second catalyst may have a ratio $A_2/A_1$ of 0.03 or more of an amount $A_2$ of acid sites measured in a temperature range of 600° C. or higher to an amount $A_1$ of all acid sites measured by ammonia temperature programmed desorption.

The second catalyst may include silica and alumina, and a molar ratio of Si to Al (Si/Al) in the second catalyst may be 100 or more.

Assuming that a mass content of the branched olefin in the raw material is $C_1$ and a mass content of the straight chain olefin in the raw material is $C_2$, $C_2/C_1$ may be 0.1 to 5.0.

The straight chain olefin may include butene.

The raw material may be obtained by fluid catalytic cracking of a heavy oil fraction, and the number of carbon atoms of the branched olefin or the straight chain olefin may be 4.

The raw material may be obtained by thermal decomposition of naphtha, and the number of carbon atoms of the branched olefin or the straight chain olefin may be 4.

Advantageous Effects of Invention

According to the present invention, diene can be produced in a high yield by using a raw material including a branched olefin and a straight chain olefin.

DESCRIPTION OF EMBODIMENTS

A preferred embodiment of the present invention will now be described. It is noted that the present invention is not limited to the following embodiment at all.

A method for producing diene according to the present embodiment includes at least a step 1 and a step 2.

In the step 1, from a raw material including at least a branched olefin and a straight chain olefin, the branched olefin is removed to obtain a straight chain internal olefin. In the step 2, diene is produced from the internal olefin by oxidative dehydrogenation using a first catalyst and a second catalyst. The first catalyst has a complex oxide including bismuth, molybdenum and oxygen. The second catalyst includes at least one selected from the group consisting of silica and alumina. An internal olefin refers to a monoolefin having a double bond in a carbon chain, and is a monoolefin except for a terminal olefin. A terminal olefin refers to a monoolefin having a double bond at the end of a carbon chain. The first catalyst has activity to oxidatively dehydrogenate a terminal olefin. The second catalyst has activity to isomerize an internal olefin to a terminal olefin.

According to the method for producing diene of the present embodiment, even if the raw material includes a branched olefin and a straight chain olefin, a diene corresponding to the straight chain olefin can be obtained in a high yield. In other words, the yield of diene in oxidative dehydrogenation can be improved.

The yield of diene may be defined, for example, by the following expression 1:

$$r_Y(\%) = m_P/m_{O1} \times 100 \qquad (1)$$

wherein $m_P$ represents a concentration of diene in a product obtained in the step 2; and $m_{O1}$ represents a sum of concentrations of an internal olefin in a reactant (an in-process oil A described later) to be used in the step 2.

The oxidative dehydrogenation of a monoolefin proceeds, for example, through the following reaction path: First, the monoolefin comes into contact with and adsorbs onto a metal oxide (a dehydrogenation catalyst). Next, oxygen in the lattice of the metal oxide pulls out two hydrogen atoms from the adsorbed monoolefin, and thus, the monoolefin is dehydrogenated. As a result, a diene corresponding to the monoolefin and water are produced. Specifically, a diene having the same number of carbon atoms as the monoolefin is produced. After the oxidative dehydrogenation, the resultant oxygen vacancies in the lattice of the metal oxide are filled with molecular oxygen supplied together with the monoolefin.

It is presumed that a high diene yield can be attained in the present embodiment for the following reason:

When a raw material including a branched olefin is subjected to the oxidative dehydrogenation, there may arise problems, for example, that an unwanted byproduct is produced in addition to diene, that the amount of consumed oxygen is increased, and that a dehydrogenation catalyst is deactivated. These problems are suppressed by removing the branched olefin in the step 1. Besides, when a dehydrogenation catalyst including bismuth and molybdenum in particular is used, the oxidative dehydrogenation of the internal olefin obtained in the step 1 is difficult to proceed as compared with the oxidative dehydrogenation of a terminal olefin. This is probably because the internal olefin has a double bond inside a carbon chain, and hence is more difficult to be adsorbed onto the dehydrogenation catalyst than the terminal olefin. In the present embodiment, the internal olefin is isomerized to a terminal olefin by a second catalyst (an isomerization catalyst) in the step 2, and this terminal olefin is oxidatively dehydrogenated by the first catalyst (the dehydrogenation catalyst) to produce diene. If the second catalyst is not used but the first catalyst alone is used in the step 2, it is difficult to produce diene in a sufficient yield.

It is presumed that the diene yield is improved through the above-described mechanism. The reason for the improvement of the diene yield is, however, not limited to the above-described reason.

Now, the step 1 and the step 2 will be described in detail.

<Step 1>

The raw material used in the step 1 includes a branched olefin and a straight chain olefin. The number of carbon atoms of the branched olefin may be, for example, 4 to 10, or 4 to 6. The number of carbon atoms of the straight chain olefin may be, for example, 4 to 10, or 4 to 6. The number of carbon atoms of the branched olefin may be the same as the number of carbon atoms of the straight chain olefin. The number of carbon atoms of the branched olefin may be different from the number of carbon atoms of the straight chain olefin. The number of carbon atoms of the straight chain olefin may be the same as the number of carbon atoms of a diene to be produced. In other words, the straight chain olefin may be a monoolefin obtained by hydrogenating one of double bonds present in the diene presumed as a product of the step 2.

Assuming that a mass content of all branched olefins in the raw material is $C_1$ and that a mass content of all straight chain olefins in the raw material is $C_2$, $C_2/C_1$ may be 0.1 to 5.0, 0.1 to 3.0, or 0.5 to 3.0. In other words, $C_2/C_1$ may be 0.1 or more, or 0.5 or more. Besides, $C_2/C_1$ may be 5.0 or less, or 3.0 or less. As $C_2/C_1$ is larger, the diene yield is more easily increased.

The branched olefin may be, for example, at least one selected from the group consisting of isobutene, 2-methyl-1butene, 2-methyl-2butene, 3-methyl-1butene, 2-methyl-1pentene, 3-methyl-1pentene, 2-methyl-2-pentene and 3-methyl-2-pentene.

The straight chain olefin may be a terminal olefin, or an internal olefin. When an internal olefin is not produced by removing the branched olefin in the step 1, at least a part of the straight chain olefins included in the raw material is an internal olefin. When the branched olefin is removed by, for example, a sulfuric acid absorption process in which a terminal olefin is not isomerized, the raw material originally includes an internal olefin. On the other hand, if an internal olefin is produced from the straight chain olefin by removing the branched olefin, the raw material may originally include a terminal olefin, and need not include an internal olefin. When the branched olefin is removed by, for example, reactive distillation in which a terminal olefin is isomerized, the raw material may originally include a terminal olefin, and need not include an internal olefin. When an internal olefin is produced from a terminal olefin by removing the branched olefin, all the straight chain olefins included in the raw material may be terminal olefins. The raw material may include both a terminal olefin and an internal olefin.

The terminal olefin may be, for example, at least one selected from the group consisting of 1-butene, 1-pentene, 1-hexene, 1-octene and 1-decene. The internal olefin may be, for example, at least one selected from the group consisting of trans-2-butene, cis-2-butene, 2-pentene, 2-hexene, 3-hexene, 2-octene, 3-octene, 4-octene, 2-decene, 3-decene, 4-decene and 5-decene. The raw material may include two or more terminal olefins, and two or more internal olefins.

If the straight chain olefin is butene, the diene yield is easily improved. In other words, if the internal olefin obtained in the step 1 is 2-butene, 1-butene is easily produced by isomerization of the 2-butene in the step 2, and hence, 1,3-butadiene is easily obtained in a high yield by the oxidative dehydrogenation of the 1-butene.

The raw material may include, as long as the effects of the present invention are not impaired, an impurity such as hydrogen, carbon monoxide, carbon dioxide gas, water, a saturated hydrocarbon compound or a diene. The saturated hydrocarbon compound may be, for example, at least one selected from the group consisting of methane, ethane, propane, n-butane, cyclobutane and isobutane. If the raw material includes a branched saturated hydrocarbon such as isobutane, the branched saturated hydrocarbon can be removed in the step 1.

The raw material may be a hydrocarbon oil obtained by fluid catalytic cracking of a heavy oil fraction. The number of carbon atoms of a branched olefin or a straight chain olefin included in the hydrocarbon oil may be 4. In other words, the raw material may include a C4 fraction obtained by the fluid catalytic cracking of a heavy oil fraction. The term "C4 fraction" refers to a fraction including, as a principal component, a hydrocarbon having a number of carbon atoms of 4. The raw material may consist of the C4 fraction alone. The C4 fraction may include at least one of 1-butene and 2-butene, and isobutene. If the raw material includes a C4 fraction obtained by the fluid catalytic cracking of a heavy oil fraction, the effects of the present invention are easily obtained. A C4 fraction is comparatively inexpensively available.

The raw material may be a hydrocarbon oil obtained by thermal decomposition of naphtha. The number of carbon atoms of a branched olefin or a straight chain olefin included in the hydrocarbon oil may be 4. In other words, the raw material may be a C4 fraction obtained by the thermal decomposition of naphtha. The raw material may consist of merely a C4 fraction obtained by the thermal decomposition of naphtha. A hydrocarbon oil obtained by separating butadiene from a C4 fraction obtained by the thermal decomposition of naphtha may be used as the raw material. If the raw material includes a C4 fraction obtained by the thermal decomposition of naphtha, the effects of the present invention are easily obtained. A C4 fraction is comparatively inexpensively available.

A method for removing the branched olefin from the raw material in the step 1 is not especially limited. The method for removing the branched olefin from the raw material in the step 1 may be, for example, at least one method selected from the group consisting of reactive distillation (isomerization distillation process), gas adsorption separation process, sulfuric acid absorption process, etherification process and dimerization process. The gas adsorption separation process is a method in which the branched olefin is separated from the raw material by causing the branched olefin included in the raw material in a gas phase to be selectively adsorbed by an adsorbent. The sulfuric acid absorption process is a method in which the branched olefin is separated from the raw material by causing the branched olefin included in the raw material to be selectively absorbed by sulfuric acid. The etherification process is a method in which the branched olefin included in the raw material is reacted with alcohol to form an ether, and the ether is separated from the raw material by distillation. The dimerization process is a method in which the branched olefin included in the raw material is dimerized, and the thus obtained dimer is separated from the raw material by distillation.

If the branched olefin is removed by employing at least one method selected from the group consisting of the gas adsorption separation process, the sulfuric acid absorption process, the etherification process and the dimerization process, the isomerization of the terminal olefin need not be caused in the step 1, and the internal olefin need not be produced. If the terminal olefin is not isomerized in the step 1, the internal olefin obtained in the step 1 is derived from an internal olefin originally included in the raw material.

On the other hand, in employing the reactive distillation (the isomerization distillation process), the branched olefin is removed from the raw material, and in addition, the terminal olefin present in the raw material is isomerized to the internal olefin. Now, the details of the reactive distillation performed in the step 1 will be described.

In the reactive distillation, an isomerization catalyst having activity to isomerize the terminal olefin present in the raw material to the internal olefin is used. The isomerization catalyst used in the reactive distillation performed in the step 1 is designated as the "first isomerization catalyst". On the other hand, the second catalyst used in the step 2 is designated as the "second isomerization catalyst" in some cases.

In the reactive distillation, a distillation column (a reactive distillation column) in which the first isomerization catalyst is placed is used. The raw material is supplied to the reactive distillation column to be brought into contact with the first isomerization catalyst, and thus, the terminal olefin present in the raw material is isomerized to produce the internal olefin. At substantially the same time as the isomerization, the internal olefin and the branched olefin and other components derived from the raw material are distilled. The boiling point of the internal olefin tends to be higher than the boiling point of the branched olefin. Accordingly, a fraction including the internal olefin (a fraction A) is collected from the bottom of the column by the distillation. On the other hand, a fraction including the branched olefin (a fraction B) is collected from the top of the column.

As described so far, in the reactive distillation, the terminal olefin present in the raw material is isomerized to the internal olefin, and the branched olefin present in the raw material is separated/removed from the internal olefin and the other components by the distillation. In other words, the isomerization reaction and the distillation are substantially simultaneously performed in the reactive distillation.

If the raw material includes a terminal olefin and a branched olefin having close boiling points, the branched olefin can be easily removed by the reactive distillation performed in the step 1. If the raw material includes, for example, 1-butene and isobutene, the boiling point of 1-butene (for example, −6.6° C. at 1 atm) and the boiling point of isobutene (for example, −6.9° C. at 1 atm) are substantially equivalent. Therefore, it is difficult to separate 1-butene and isobutene from each other by distillation. On the other hand, in the reactive distillation performed in the step 1, 1-butene is isomerized to 2-butene. The boiling point of cis-2-butene (for example, 3.7° C. at 1 atm) and the boiling point of trans-2-butene (for example, 0.9° C. at 1 atm) are both higher than the boiling point of isobutene. Therefore, in the reactive distillation, a fraction including 2-butene (a fraction A) is collected from the bottom of the column, and a fraction including isobutene (a fraction B) is collected from the top of the column.

The temperature in the top of the reactive distillation column may be adjusted in accordance with the boiling point of the branched olefin. The temperature in the bottom of the reactive distillation column may be adjusted in accordance with the boiling point of the internal olefin produced from the straight chain olefin. The temperature of the first isomerization catalyst (the reaction temperature of the isomerization) may be adjusted in accordance with the type of the terminal olefin to be isomerized. For example, if 1-butene present in the raw material is to be isomerized to produce 2-butene, the temperature of the first isomerization catalyst (the reaction temperature of the isomerization) may be 20 to 150° C., the air pressure within the reactive distillation column may be 0 to 5.0 MPaG, and the temperature in the column top may be 20 to 150° C.

In the reactive distillation performed in the step 1, the raw material may be gasified before being supplied to the reactive distillation column. Alternatively, the raw material in a liquid form may be supplied to the reactive distillation column.

The first isomerization catalyst is not especially limited as long as it has activity to isomerize the terminal olefin to the internal olefin. The first isomerization catalyst may include, for example, at least one metal selected from the group consisting of palladium (Pd), nickel (Ni), platinum (Pt), copper (Cu) and silver (Ag). The first isomerization catalyst may be fixed as a catalyst layer in the reactive distillation column. A reaction vessel filled with the first isomerization catalyst may be placed within the reactive distillation column.

The fraction A obtained by the reactive distillation performed in the step 1 may include a component except for the internal olefin. For example, the fraction A may include the branched olefin that has not been removed but remains after the step 1. If the fraction A includes the branched olefin, the branched olefin may be removed from the fraction A by supplying the fraction A as the raw material again to the reactive distillation column. The fraction A may include the terminal olefin that has not been isomerized and remains after the step 1. The fraction A may include a hydrocarbon derived from the raw material, or a byproduct of the isomerization reaction. The fraction A may include, for example, hydrogen, carbon monoxide, carbon dioxide gas, methane or a diene.

The number of carbon atoms of the internal olefin obtained in the step 1 may be the same as the number of carbon atoms of the diene of interest. The number of carbon atoms of the internal olefin may be 4 to 10, or 4 to 6.

The internal olefin may be a straight chain unsaturated hydrocarbon. The straight chain unsaturated hydrocarbon may be, for example, at least one selected from the group consisting of trans-2-butene, cis-2-butene, 2-pentene, 2-hexene, 3-hexene, 2-octene, 3-octene, 4-octene, 2-decene, 3-decene, 4-decene and 5-decene.

The internal olefin may have a substituent including a hetero atom such as oxygen, nitrogen, halogen or sulfur. Such a substituent may be, for example, at least one selected from the group consisting of a halogen atom (—F, —Cl, —Br or —I), a hydroxyl group (—OH), an alkoxy group (—OR (wherein R represents a hydrocarbon group)), a carboxyl group (—COOH), an ester group (—COOR (wherein R represents a hydrocarbon group)), an aldehyde group (—CHO) and an acyl group (—C(=O)R). The raw material including the internal olefin having the substituent may be, for example, an alcohol, an ether, or a biofuel.

Hereinafter, the hydrocarbon including the internal olefin obtained in the step 1 is designated as the "in-process oil A". The in-process oil A may consist of the internal olefin alone. The in-process oil A may be the fraction A obtained by the reactive distillation in the step 1. If a mixture including the internal olefin and other components is obtained without performing the reactive distillation in the step 1, the mixture may be used as the in-process oil A. A slight amount of the branched olefin may remain in the in-process oil A. The in-process oil A may include the terminal olefin in addition to the internal olefin.

<Step 2>

In the step 2, the internal olefin obtained in the step 1 is isomerized by the second catalyst (the second isomerization catalyst) to produce a terminal olefin, and the terminal olefin produced by the isomerization is oxidatively dehydrogenated by the first catalyst (the dehydrogenation catalyst) to produce diene. The second isomerization catalyst used in the step 2 is different from the first isomerization catalyst used in the step 1. In the step 2, a terminal olefin originally included in the in-process oil A may be oxidatively dehydrogenated to produce diene.

The first catalyst (the dehydrogenation catalyst) has a complex oxide including bismuth (Bi), molybdenum (Mo) and oxygen. When the dehydrogenation catalyst has the complex oxide including bismuth, molybdenum and oxygen, the terminal olefin is oxidatively dehydrogenated by the first catalyst to produce diene.

The composition of the complex oxide is not especially limited. The complex oxide may consist of merely bismuth, molybdenum and oxygen. The complex oxide may include an additional component in addition to bismuth, molybdenum and oxygen. The additional component may be, for example, at least one selected from the group consisting of cobalt (Co), nickel (Ni), iron (Fe), magnesium (Mg), calcium (Ca), zinc (Zn), cerium (Ce), samarium (Sm), sodium (Na), potassium (K), rubidium (Rb), cesium (Cs), thallium (Tl), boron (B), phosphorus (P), arsenic (As) and tungsten (W).

The first catalyst (the dehydrogenation catalyst) may consist of merely the complex oxide including bismuth, molybdenum and oxygen. The first catalyst (the dehydrogenation catalyst) may include a component except for the complex oxide. Besides, the first catalyst (the dehydrogenation catalyst) may contain a molding aid as long as the physical properties and the catalyst performance of the catalyst are not impaired. The molding aid may be, for example, at least one selected from the group consisting of a thickener, a surfactant, a water retention agent, a plasticizer and a binder material.

The second catalyst includes at least one selected from the group consisting of silica and alumina. When the second catalyst includes at least one selected from the group consisting of silica and alumina, the internal olefin is isomerized in the step 2 to improve the diene yield. The second catalyst may consist of silica-alumina alone.

The second catalyst may have a support and an element supported on the support (hereinafter sometimes referred to as the "supported element").

The support may include at least one selected from the group consisting of silica and alumina. The support may be one or a plurality selected from the group consisting of silica, alumina, silica-alumina, zeolite, activated clay, diatomite and kaolin. The support may further include activated carbon. The support may consist of zeolite alone. A crystalline aluminosilicate generally designated as zeolite has a minute space (a nano-space) of a molecular size in one crystal. The zeolite is classified in accordance with its crystal structure, and there are a large number of types of zeolites such as LTA (A type), MFI (ZSM-5 type), MOR, FER and FAU (X type and Y type) zeolites.

The zeolite may be a faujasite zeolite. The faujasite zeolite is a zeolite expressed as an FAU structure among skeletal structure types in accordance with the IUPAC recommendation. When the second catalyst has the support including the faujasite zeolite, the internal olefin is easily isomerized in the step 2, and the diene yield is easily improved. It is presumed that the second catalyst including the faujasite zeolite has high isomerization activity because a large amount of supported element (active metal) is highly dispersed in the faujasite zeolite.

The faujasite zeolite may be, for example, at least one selected from the group consisting of X type zeolite, Y type zeolite and USY type zeolite. The faujasite zeolite may be at least one selected from the group consisting of H type, $NH_4$ type, Na type, Li type, K type, Rb type, Cs type, Fr type, Be type, Mg type, Ca type, Sr type, Ba type and Ra type. Any of these types of faujasite zeolites can be used. The faujasite zeolite may be, for example, at least one selected from the group consisting of HY type zeolite, NH$_4$Y type zeolite, NaY type zeolite, LiY type zeolite, KY type zeolite, RbY type zeolite, CsY type zeolite, FrY type zeolite, BeY type zeolite, MgY type zeolite, CaY type zeolite, SrY type zeolite, BaY type zeolite, RaY type zeolite, HX type zeolite, NH$_4$X type zeolite, NaX type zeolite, LiX type zeolite, KX type zeolite, RbX type zeolite, CsX type zeolite, FrX type zeolite, BeX type zeolite, MgX type zeolite, CaX type zeolite, SrX type zeolite, BaX type zeolite and RaX type zeolite. Any of these types of faujasite zeolites can be used. Such a faujasite zeolite can be prepared by, for example, ion exchange of a metal element (a cation) included in the faujasite zeolite. In the present embodiment, when the support includes X type zeolite, the internal olefin is easily isomerized in the step 2 and the diene yield is easily improved. Since X type zeolite has a comparatively large number of ion exchange sites, the amount of supported element (for example, the amount of Ag) per unit volume in the X type zeolite can be large. Accordingly, if the X type zeolite is used, the internal olefin is easily isomerized in the step 2, and the diene yield is easily improved. A part or the whole of cations (such as H$^+$, NH$_4^+$, Na$^+$, Li$^+$, K$^+$, Rb$^+$, Cs$^+$, Fr$^+$, Be$^{2+}$, Mg$^{2+}$, Ca$^{2+}$, Sr$^{2+}$, Ba$^{2+}$ and Ra$^{2+}$) of the faujasite zeolites may be substituted by the supported element.

The supported element of the second catalyst may be at least one element selected from the group consisting of Group 10 elements of the periodic table and Group 11 elements of the periodic table, and lanthanoids: The periodic table refers to a long period periodic table of elements defined by IUPAC (International Union Pure and Applied Chemistry). The supported element may be an element except for Group 10 elements and Group 11 elements of the periodic table, and lanthanoids.

Group 10 elements of the periodic table may be, for example, at least one selected from the group consisting of nickel (Ni), palladium (Pd) and platinum (Pt). Group 11 elements of the periodic table may be, for example, at least one selected from the group consisting of copper (Cu), silver (Ag) and gold (Au). Lanthanoids may be, for example, at least one selected from the group consisting of Lanthanum (La) and cerium (Ce). The element supported on the support may be a combination of these elements. It is preferable for the element supported on the support to be Ag. When Ag is supported on the support, the internal olefin is easily isomerized in the step 2, and the diene yield is easily improved.

A suitable aspect of the second catalyst will now be described.

The second catalyst of this aspect includes silica and alumina. Here, the term "include silica and alumina" means that Si and Al are included as inorganic oxides, embracing a complex oxide (such as silica-alumina or zeolite).

A conventional isomerization reaction for an olefin is generally performed under environment where oxygen is absent, and if oxygen is present, it is difficult to cause the isomerization of an olefin to selectively proceed because a large number of side reactions including a complete oxidation reaction occur. On the other hand, in using the second catalyst of the present embodiment, side reactions are sufficiently suppressed, and hence, the isomerization reaction for an olefin can be efficiently caused to proceed even in the step 2 where oxygen is present. Besides, in using the second catalyst of this aspect corresponding to a suitable aspect, this effect is more remarkably exhibited, and in addition, since the durability of the catalyst is excellent, the isomerization reaction can be performed for a long period of time.

In this aspect, the second catalyst may be a catalyst including one of, or two or more inorganic oxides selected from the group consisting of silica-alumina and zeolites, and may be a catalyst consisting of the inorganic oxide. Examples of the zeolites include those mentioned above, and the second catalyst may include one or more zeolites, or two or more zeolites.

In the second catalyst of this aspect, a molar ratio of Si to Al (Si/Al) may be 5.0 or more, 100 or more, or 200 or more. Besides, the molar ratio (Si/Al) may be 10000 or less, 3000 or less, or 2000 or less. If the ratio falls in such a range, the degradation of the second catalyst tends to be suppressed.

In the second catalyst of this aspect, a metal element may be supported on the above-described inorganic oxide. The metal element to be supported (hereinafter sometimes referred to as the supported metal element) is not especially limited, and may be, for example, an alkali metal, an alkali earth metal or a transition metal.

A method for supporting the supported metal element is not especially limited, and for example, an impregnation method, a deposition method, a coprecipitation method, a kneading method, an ion exchange method or a pore filling method may be employed.

A supply source of the supported metal element may be, for example, at least one selected from the group consisting of an oxide, a nitrate, a carbonate, an ammonium salt, a hydroxide, a carboxylate, a carboxylic acid ammonium salt, a halogenated ammonium salt, a hydroacid (for example, chloroplatinic acid (H$_2$PtCl$_6$), an acetylacetonate and an alkoxide.

The content of the supported metal element in the second catalyst of this aspect is not especially limited, and may be, for example, 0.01 to 100 parts by mass, or 0.1 to 50 parts by mass with respect to 100 parts by mass of the inorganic oxide. It is noted that the content of the supported metal element can be obtained by inductively coupled plasma atomic emission spectrophotometry (ICP emission spectrophotometry).

As an effective method for characterizing the acidity of a catalyst, ammonia temperature programmed desorption (ammonia TPD, NH$_3$-TPD) is widely known. For example, C. V. Hidalgo et al., Journal of Catalysis, vol. 85, pp. 362-369 (1984) describes that the amount of Bronsted acid sites or an acid strength distribution of Bronsted acid sites can be measured by the ammonia TPD.

In the ammonia TPD, ammonia, that is, a basic probe molecule, is caused to be adsorbed to a sample solid, and the temperature is continuously increased to measure the amount of desorbed ammonia and the temperature at the same time. Ammonia adsorbed to a weak acid site is desorbed at a low temperature (corresponding to desorption in a region where heat of adsorption is low), and ammonia adsorbed to a strong acid site is desorbed at a high temperature (corresponding to desorption in a region where the heat of adsorption is high). In the ammonia TPD, the acid strength is expressed based on the temperature and the amount of heat of adsorption without using a coloring reaction, and hence, a solid acid strength and a solid acid amount can be obtained as more accurate values, and thus, the characteristics of a catalyst can be appropriately evaluated.

The amount of acid sites (the acid amount) of the second catalyst can be obtained by the ammonia TPD in which an ammonia adsorption amount is measured by employing an apparatus and measurement conditions described in "Niwa; Zeolite, 10, 175 (1993)".

In this aspect, an amount $A_1$ of all the acid sites (the total acid amount) of the second catalyst may be 0.11 mmol/g or less, 0.09 mmol/g or less, 0.03 mmol/g or less, 0.015 mmol/g or less, or 0.010 mmol/g or less. If the total acid amount falls in the above-described range, there is a tendency that side reactions such as skeletal isomerization and $CO_2$ production, and degradation of the catalyst through coke deposition are suppressed. Besides, the total acid amount $A_1$ of the second catalyst of this aspect may be 0.001 mmol/g or more, or 0.003 mmol/g or more.

In the second catalyst of this aspect, a ratio $A_2/A_1$ of the amount $A_2$ of acid sites measured in a temperature range of 600° C. or more to the total acid amount $A_1$ may be 0.03 or more, 0.05 or more, 0.08 or more, 0.1 or more, or 0.15 or more. If the ratio $A_2/A_1$ falls in the above-described range, there is a tendency that the side reactions such as skeletal isomerization and $CO_2$ production, and the degradation of the catalyst through the coke deposition are suppressed. Besides, the ratio $A_2/A_1$ may be 1.0 or less, or 0.7 or less.

The second catalyst of this aspect may be calcined if necessary. The calcination may be performed in one stage or multiple stages of two or more stages. The calcination temperature is not especially limited. If the calcination is performed in one stage, the calcination temperature may be, for example, 200 to 600° C. The calcination time may be 1 to 10 hours. The calcination may be generally performed under airstream, but the atmosphere employed in the calcination is not especially limited.

From the viewpoint of improving moldability, the second catalyst of this aspect may contain a molding aid as long as the physical properties and the catalyst performance of the catalyst are not impaired. The molding aid may be, for example, at least one selected from the group consisting of a thickener, a surfactant, a water retention agent, a plasticizer and a binder material.

The second catalyst of this aspect may be molded by an extrusion molding method, a tablet molding method or the like. The molding process may be performed at an appropriate stage during the production of the catalyst in consideration of the reactivity and the like of the molding aid.

The shape of the second catalyst of this aspect is not especially limited, and can be appropriately selected in accordance with the form where the catalyst is used. The second catalyst may be in the shape of, for example, a pellet, a granule, a honeycomb, a sponge or the like.

In the step 2, a reaction vessel filled with the first catalyst (the dehydrogenation catalyst) and the second catalyst (the second isomerization catalyst) may be used to produce the terminal olefin by the isomerization of the internal olefin, and the terminal olefin may be oxidatively dehydrogenated to produce diene.

A reaction system employed in the step 2 is not especially limited. The reaction system may be, for example, a fixed bed system, a moving bed system or a fluidized bed system. If the isomerization of the internal olefin and the oxidative dehydrogenation of the terminal olefin are performed by employing the fixed bed system, the process design can be easily performed.

The reaction performed in the step 2 may be a gas phase reaction. Specifically, the in-process oil A including the internal olefin is first gasified by using a vaporizer or the like. Next, the gaseous in-process oil A and a molecular oxygen-containing gas are heated to about 150 to 250° C. using a preheater or the like, and the resultant gases are supplied into the reaction vessel. In other words, the oxidative dehydrogenation of the terminal olefin may be performed in the presence of the molecular oxygen-containing gas. The in-process oil A and the molecular oxygen-containing gas may be supplied to the reaction vessel after preheating in a mixed state, namely, in the form of a mixed gas. The in-process oil A and the molecular oxygen-containing gas may be separately preheated before being supplied to the reaction vessel through separate tubes. If the in-process oil A and the molecular oxygen-containing gas are mixed to be preheated and then supplied to the reaction vessel, these gases are homogeneously mixed. Therefore, a phenomenon in which heterogeneously mixed gases produce a detonating gas in a reaction vessel is suppressed. Besides, a situation where raw materials having different compositions are supplied through different tubes of a multi-tubular reaction vessel is difficult to occur.

The gaseous in-process oil A and the molecular oxygen-containing gas are supplied to the reaction vessel, and at the same time, a nitrogen gas and water (water vapor) may be supplied to the reaction vessel. By adjusting the amount of the nitrogen gas and water (water vapor) to be supplied, the concentrations of a combustible gas such as the in-process oil A and the molecular oxygen in a gas (a reaction gas) supplied to the reaction vessel can be adjusted. In this manner, the production of a detonating gas within the reaction vessel can be easily suppressed. Besides, when water (water vapor) is supplied to the reaction vessel, the coking of the catalyst within the reaction vessel can be easily suppressed. The nitrogen gas and water (water vapor) may be mixed with the gaseous in-process oil A and the molecular oxygen-containing gas before preheating the gaseous in-process oil A. The nitrogen gas and water (water vapor) may be separately preheated before being directly supplied to the reaction vessel through separate tubes.

The composition of the reaction gas may be controlled so that the composition of the reaction gas does no fall in an explosive range at the inlet of the reaction vessel. The composition of the reaction gas may be controlled while monitoring flow rates of the respective gases included in the reaction gas. The flow rates of the respective gases can be monitored, for example, by providing a flowmeter in each tube used for supplying each of the gases. The explosive range refers to a composition range in which a mixed gas (the reaction gas) of oxygen (the molecular oxygen) and a combustible gas (the gaseous in-process oil A) ignites in the presence of some ignition source. Besides, the highest concentration of the combustible gas at which the mixed gas ignites is designated as an upper explosive limit. The lowest concentration of the combustible gas at which the mixed gas ignites is designated as a lower explosive limit. If the concentration of the combustible gas in the mixed gas is not less than the upper explosive limit or not more than the lower explosive limit, the mixed gas does not ignite. Furthermore, an oxygen concentration at which the upper explosive limit and the lower explosive limit have the same value is designated as a limiting oxygen concentration. If the oxygen concentration is lower than the limiting oxygen concentration, the mixed gas does not ignite regardless of the concentration of the combustible gas.

The composition of the reaction gas at the inlet of the reaction vessel and the reaction conditions may be adjusted so that the composition of a product (a product gas) at the outlet of the reaction vessel does not fall in the explosive range. Besides, the composition of the reaction gas at the inlet of the reaction vessel and the reaction conditions may be adjusted so that an oxygen concentration in the product gas can be lower than the limiting oxygen concentration. Specifically, the oxygen flow rate may be adjusted so that the oxygen concentration in the reaction gas can be 11% by volume or less. The oxygen concentration in the reaction gas may be measured with an oxygen analyzer provided at the inlet of the reaction vessel.

At the beginning of the supply of the reaction gas, the composition of the reaction gas may be adjusted so that the oxygen concentration in the reaction gas can be lower than the limiting oxygen concentration. Besides, as the reaction proceeds, the amounts of the material gas and the molecular oxygen-containing gas supplied may be increased so as to adjust the composition of the reaction gas in such a manner that the concentration of the material gas in the reaction gas can be higher than the upper explosive limit.

The temperature within the reaction vessel (the reaction temperature) is not especially limited. The reaction temperature may be, for example, 280 to 400° C. If the reaction temperature is 280° C. or more, a sufficient diene yield tends to be obtained because equilibrium conversion of the terminal olefin does not become too low. If the reaction temperature is 400° C. or less, high activities of the first catalyst and the second catalyst can be easily retained for a long period of time because the coking rate thereof is suppressed.

The pressure within the reaction vessel (the air pressure in the reaction vessel) is not especially limited. The air pressure in the reaction vessel may be, for example, 0 MPaG or more, 0.02 MPaG or more, or 0.05 MPaG or more. As the air pressure in the reaction vessel is higher, the amount of the reaction gas that can be supplied to the reaction vessel is larger. Besides, the air pressure in the reaction vessel may be, for example, 0.5 MPaG or less, 0.3 MPaG or less, or 0.1 MPaG or less. As the air pressure in the reaction vessel is lower, the explosive range tends to be smaller.

The weight hourly space velocity (WHSV) in the reaction vessel may be 0.01 to 50 $h^{-1}$, or 0.05 to 10 $h^{-1}$. Here, the WHSV refers to a ratio (F/W) of a supply rate F (amount supplied/time) of the gaseous in-process oil A to the mass W (catalyst mass) of the first catalyst and the second catalyst in a continuous reactor. If the WHSV is 50 $h^{-1}$ or lower, the gaseous in-process oil A can be brought into contact with the catalysts for a sufficient time period, and hence, the isomerization of the internal olefin and the oxidative dehydrogenation of the terminal olefin can easily proceed. If the WHSV is 0.01 $h^{-1}$ or more, the decomposition of a hydrocarbon compound does not excessively proceed, and hence, the diene yield can be easily improved.

The content of the molecular oxygen in the molecular oxygen-containing gas may be 10% by volume or more, 15% by volume or more, or 20% by volume or more. Incidentally, from the viewpoint of cost necessary for industrially preparing the molecular oxygen-containing gas, the content of the molecular oxygen in the molecular oxygen-containing gas may be 50% by volume or less, 30% by volume or less, or 1% by volume or less.

The molecular oxygen-containing gas may include an arbitrary impurity as long as the effects of the present invention are not impaired. Such an impurity may be, for example, nitrogen, argon, neon, helium, carbon monoxide, carbon dioxide or water. The molecular oxygen-containing gas may be, for example, air. The content of nitrogen in the molecular oxygen-containing gas may be 90% by volume or less, 85% by volume or less, or 80% by volume or less. The content of an impurity except for nitrogen may be 10% by volume or less, or 1% by volume or less. If the contents of these impurities are too large, there is a tendency that the molecular oxygen in an amount necessary for the reaction is difficult to supply.

As long as the effects of the present invention are not impaired, the isomerization of the internal olefin and the oxidative dehydrogenation of the terminal olefin can be performed in the presence of the internal olefin (the in-process oil A), the molecular oxygen-containing gas, nitrogen gas, water (water vapor) and an additional component. The additional component may be, for example, methane, hydrogen or carbon dioxide.

The first catalyst (the dehydrogenation catalyst) and the second catalyst (the second isomerization catalyst) may be separately placed in the reaction vessel. In other words, the reaction vessel may be provided with a catalyst layer including the first catalyst and another catalyst layer including the second catalyst. Alternatively, a mixture including the first catalyst and the second catalyst may be used. In other words, the reaction vessel may be provided with a catalyst layer including the first catalyst and the second catalyst.

A ratio between the volume of the first catalyst and the volume of the second catalyst (the volume of the first catalyst/the volume of the second catalyst) may be 1.5 to 20. If the volume ratio falls in this range, the diene yield can be easily improved.

The product (the product gas) of the step 2 may include a component except for the diene of interest. The product of the step 2 may include, for example, a hydrocarbon derived from the in-process oil A, the first catalyst, the second catalyst or a byproduct. The byproduct may be, for example, water, an oxygen-containing compound, a light olefin, or an olefin polymer. The oxygen-containing compound may be, for example, carbon monoxide or carbon dioxide. The light olefin may be, for example, ethylene or propylene. Such an impurity may be separated from the product by any known method.

The diene obtained in the step 2 may be, for example, at least one selected from the group consisting of 1,3-butadiene, piperylene, isoprene, 1,5-hexadiene, 1,6-octadiene and 1,9-decadiene. Specifically, if the internal olefin obtained in the step 1 is trans-2-butene or cis-2-butene, 1,3-butadiene is likely to be obtained. If the internal olefin obtained in the step 1 is 2-pentene, piperylene is likely to be obtained. If the internal olefin obtained in the step 1 is 2-hexene or 3-hexene, 1,5-hexadiene is likely to be obtained. According to the method for producing diene of the present embodiment, a thermodynamically stable conjugated diene can be easily obtained.

1,3-Butadiene, that is, a representative example of diene, is used as a raw material of a synthetic rubber such as SBR (styrene-butadiene rubber) or NBR (acrylonitrile-butadiene rubber), or a raw material of an ABS (acrylonitrile butadiene styrene) resin or the like.

According to the present embodiment described so far, even if a raw material including a branched olefin and a straight chain olefin is used, the diene yield is improved as compared with that obtained by a conventional production method.

EXAMPLES

Now, the present invention will be described in more detail with reference to examples and a comparative example, and it is noted that the present invention is not limited to these examples at all.

(Preparation of First Catalyst)

A first catalyst (a dehydrogenation catalyst) was prepared as follows.

To 250 ml of pure water, 54 g of ammonium paramolybdate was added to be dissolved therein by heating to 70° C., and thus, a solution A was obtained. Next, to 60 ml of pure water, 7.18 g of ferric nitrate, 31.8 g of cobalt nitrate and 31.8 g of nickel nitrate were added to be dissolved therein by heating to 70° C., and thus, a solution B was obtained. The solution B was gradually added to the solution A under sufficiently stirring the solution A, and thus, a mixed solution of the solution A and the solution B was obtained. Next, 64 g of silica was added to the thus obtained mixed solution, and the resultant was sufficiently stirred to obtain a slurry A. The slurry A was held at 75° C. for 5 hours. Thereafter, the slurry A was dried by heating, and the resultant was heated at 300° C. for 1 hour under air atmosphere, and thus, a first granular solid (a catalyst precursor) was obtained. The loss-on-ignition of the first granular solid was 1.4% by mass.

A solution C was obtained by mixing 40.1 g of ammonium paramolybdate, 150 ml of pure water and 10 ml of ammonia water. The first granular solid was ground and dispersed in the solution C to obtain a slurry B. Next, 0.85 g of borax and 0.36 g of potassium nitrate were added to 40 ml of pure water to be dissolved therein under heating at 25° C., and thus, a solution D was obtained. The slurry B was added to the solution D, and 58.1 g of bismuth subcarbonate in which 0.45% by mass of Na had been dissolved to form a solid solution was further added thereto, followed by stirring for mixing, and thus, a slurry C was obtained. The slurry C was dried by heating at 130° C. for 12 hours to obtain a second granular solid. The second granular solid was tablet-molded using a small molding machine to obtain a tablet. The tablet had a diameter of 5 mm and a height of 4 mm. The tablet was calcined at 500° C. for 4 hours to obtain a catalyst A made of a complex oxide. The catalyst A corresponds to a first catalyst (a dehydrogenation catalyst). The catalyst A is a complex oxide including Ni, Bi Mo and O. A molar ratio among respective atoms in the catalyst A calculated based on the amounts of fed raw materials is as follows:

<Atomic Ratio>
Mo:Bi:Co:Ni:Fe:NaB:K:Si=12:5:2.5:2.5:0.4:0.35:0.2:0.08:24

(Preparation of Second Catalyst)

Synthesis Example B1

A nickel nitrate aqueous solution was prepared by adding 600 ml of distilled water to 10 g of nickel nitrate hexahydrate. Next, while stirring the nickel nitrate aqueous solution, 50 g of a NaX type zeolite molding was gradually added to the nickel nitrate aqueous solution for performing ion exchange of zeolite. The zeolite resulting from the ion exchange was washed with distilled water so as not to allow nickel nitrate to remain thereon, and then, the resultant was dried overnight in a dryer at 180° C. In this manner, a catalyst B1 corresponding to a second catalyst (a second isomerization catalyst) was obtained. The catalyst B1 is a NaX type zeolite including Ni (NiX).

Synthesis Example B2

A silver nitrate aqueous solution was prepared by adding 600 ml of distilled water to 30 g of silver nitrate. Next, while stirring the silver nitrate aqueous solution, 50 g of a NaX type zeolite molding (manufactured by Tosoh Corporation, silica-alumina ratio=2.5) was gradually added to the silver nitrate aqueous solution for performing ion exchange of zeolite. The zeolite resulting from the ion exchange was washed with distilled water so as not to allow silver nitrate to remain thereon, and then, the resultant was dried overnight in a dryer at 180° C. After the drying, the above-described ion exchange was repeated, and the resultant was washed with distilled water so as not to allow silver nitrate to remain thereon. The washed zeolite was dried overnight in a dryer at 180° C. In this manner, a catalyst B2 corresponding to a second catalyst was obtained. The catalyst B2 is a NaX type zeolite including Ag (AgX).

Example 1

<Preparation of Raw Material>

A raw material of Example 1 including the following components was prepared. Assuming that a mass content of a branched olefin (isobutene) in the raw material is $C_1$ and a mass content of straight chain olefins (1-butene, cis-2-butene and trans-2-butene) in the raw material is $C_2$, $C_2/C_1$ was 2.6.

Isobutane: 41.0% by mass
Isobutene: 13.0% by mass
1-Butene: 12.0% by mass
Normal butane: 12.0% by mass
Cis-2-butene: 9.0% by mass
Trans-2-butene: 13.0% by mass <Step 1>

Reactive distillation of the step 1 was performed as follows.

A first isomerization catalyst was fixed in a reactive distillation column. As the first isomerization catalyst, a catalyst in which 0.3 to 0.4% by mass of Pd was supported on a support of γ alumina was used. The above-described raw material was supplied to the reactive distillation column to be brought into contact with the first isomerization catalyst. A rate of the raw material fed into the reactive distillation column was set to 30 t/h. A fraction A was collected from the bottom of the reactive distillation column, and a fraction B was collected from the top of the reactive distillation column. A flow rate of the fraction A flowing out from the bottom was 14.1 t/h (corresponding to 47% by mass of the total mass of the raw material).

The thus obtained fraction A was analyzed using a gas chromatograph equipped with a flame ionization detector. Concentrations (in % by mass) of respective components in the fraction A were quantitatively determined by an absolute calibration curve method based on the gas chromatography. The composition of the fraction A (the concentrations of the respective components in the fraction A) is shown in Table 1 below. It is noted that a concentration may be also designated as a mass content (a content).

By the same method as that employed for the fraction A, the composition of the fraction B was analyzed. As a result of the analysis, it was confirmed that the fraction B mostly included isobutane and isobutene.

<Step 2>

In the step 2 of Example 1, the catalyst A and the catalyst B1 were mixed to be filled in a tubular reaction vessel. The reaction vessel was an SUS tube having an inner diameter of 14 mm and a length of 60 cm. The volume of the entire catalysts (the catalyst A and the catalyst B1) filled in the reaction vessel was 17 cc. The content of the catalyst A in the entire catalysts was adjusted to 90% by volume. The content of the catalyst B1 in the entire catalysts was adjusted to 10% by volume. The content of Ni in the entire catalysts was analyzed by the inductively coupled plasma atomic emission spectrophotometry (ICP emission spectrophotometry). The content of Ni in the entire catalysts is shown in Table 1 below.

Subsequently, the reaction vessel was connected to a flow reactor, and the temperature within the reaction vessel was increased up to 330° C. by using an electric furnace. The fraction A obtained in the step 1, air and water vapor were supplied into the reaction vessel after the temperature increased, so as to be brought into contact with the catalysts. In this manner, the oxidative dehydrogenation of the fraction A was performed within the reaction vessel. The flow rates of the fraction A, the air and the water vapor flowing into the reaction vessel were adjusted respectively to the following values:

Flow rate of fraction A: 2.16 g/h
Flow rate of air: 60 cc/min
Flow rate of water vapor: 1.5 g/h When 120 minutes had elapsed from a reaction start time, a product gas was collected from the reaction vessel. It is noted that the time when the fraction A was started to be supplied was regarded as the reaction start time (minute 0). The thus collected product gas was analyzed using a gas chromatograph equipped with a flame ionization detector. Concentrations (in % by mass) of respective components in the product gas were quantitatively determined by the absolute calibration curve method based on the gas chromatography. The concentrations of the respective components in the product gas are shown in Table 1 below. Next, on the basis of the thus determined concentrations of the respective components, a yield $R_Y$ (%) of butadiene was calculated. The yield $R_Y$ is shown in Table 1 below. It is noted that the yield $R_Y$ is defined in accordance with the following expression 1a:

$$R_Y = (M_P/M_{01}) \times 100 \qquad (1a)$$

In expression 1a, $M_P$ represents a concentration (in % by mass) of butadiene in the product gas. $M_b$ represents a sum of the concentration of cis-2-butene and the concentration of trans-2-butene in the fraction A.

Example 2

The step 1 of Example 2 was performed in the same manner as in Example 1. As a result of the analysis similar to that of Example 1, it was confirmed that a fraction A obtained in Example 2 was the same as the fraction A of Example 1. Besides, it was confirmed that a fraction B obtained in Example 2 was the same as the fraction B of Example 1.

In the step 2 of Example 2, the catalyst B2 was used as the second catalyst instead of the catalyst B1. In other words, the catalyst A and the catalyst B2 were mixed to be filled in a reaction vessel in the step 2 of Example 2. The volume of the entire catalysts (the catalyst A and the catalyst B2) filled in the reaction vessel was 17 cc. The content of the catalyst A in the entire catalysts was adjusted to 90% by volume. The content of the catalyst B2 in the entire catalysts was adjusted to 10% by volume. The content of Ni in the entire catalysts was analyzed by the ICP emission spectrophotometry. The content of Ni in the entire catalysts is shown in Table 1 below. By a similar method, the content of Ag in the entire catalysts was quantitatively determined. The content of Ag in the entire catalysts is shown in Table 1 below.

The step 2 of Example 2 was performed in the same manner as in Example 1 except for the composition of the second catalyst, and thus, a product gas of Example 2 was obtained. The product gas of Example 2 was analyzed in the same manner as in Example 1. The analysis result of Example 2 is shown in Table 1 below. A yield $R_Y$ of Example 2 calculated in the same manner as in Example 1 is shown in Table 1 below.

Example 3

The step 1 of Example 3 was performed in the same manner as in Example 1. As a result of the analysis similar to that of Example 1, it was confirmed that a fraction A obtained in Example 3 was the same as the fraction A of Example 1. Besides, it was confirmed that a fraction B obtained in Example 3 was the same as the fraction B of Example 1.

In the step 2 of Example 3, silica-alumina (a catalyst B3) was used as the second catalyst instead of the catalyst B1. In other words, the catalyst A and the catalyst B3 were mixed to be filled in a reaction vessel in the step 2 of Example 2. As the silica-alumina, IS-28 produced by JGC Catalysts and Chemicals Ltd. was used. The volume of the entire catalysts (the catalyst A and the catalyst B3) filled in the reaction vessel was 17 cc. The content of the catalyst A in the entire catalysts was adjusted to 90% by volume. The content of the catalyst B3 in the entire catalysts was adjusted to 10% by volume. The content of Ni in the entire catalysts was analyzed by the ICP emission spectrophotometry. The content of Ni in the entire catalysts is shown in Table 1 below.

The step 2 of Example 3 was performed in the same manner as in Example 1 except for the composition of the second catalyst, and thus, a product gas of Example 3 was obtained. The product gas of Example 3 was analyzed in the same manner as in Example 1. The analysis result of Example 3 is shown in Table 1 below. A yield $R_Y$ of Example 3 calculated in the same manner as in Example 1 is shown in Table 1 below.

Comparative Example 1

The step 1 of Comparative Example 1 was performed in the same manner as in Example 1. As a result of the analysis similar to that of Example 1, it was confirmed that a fraction A obtained in Comparative Example 1 was the same as the fraction A of Example 1. Besides, it was confirmed that a fraction B obtained in Comparative Example 1 was the same as the fraction B of Example 1.

In the step 2 of Comparative Example 1, a second catalyst was not used. In the step 2 of Comparative Example 1, 17 cc of the catalyst A was filled in a reaction vessel. The content of Ni in the entire catalyst (namely, the catalyst A alone) was analyzed by the ICP emission spectrophotometry. The content of Ni in the entire catalyst is shown in Table 1 below.

The step 2 of Comparative Example 1 was performed in the same manner as in Example 1 except that a second catalyst was not used, and thus, a product gas of Comparative Example 1 was obtained. The product gas of Comparative Example 1 was analyzed in the same manner as in Example 1. The analysis result of Comparative Example 1 is shown in Table 1 below. A yield $R_Y$ of Comparative Example 1 calculated in the same manner as in Example 1 is shown in Table 1 below.

TABLE 1

| | | Example 1 | | | Example 2 | | | Example 3 | | | Comparative Example 1 | | |
|---|---|---|---|---|---|---|---|---|---|---|---|---|---|
| | | Raw Material | Fraction A | Product Gas | Raw Material | Fraction A | Product Gas | Raw Material | Fraction A | Product Gas | Raw Material | Fraction A | Product Gas |
| Composition (mass %) | Isobutane | 41.0 | 0.0 | 0.0 | 41.0 | 0.0 | 0.0 | 41.0 | 0.0 | 0.0 | 41.0 | 0 | 0.0 |
| | Isobutene | 13.0 | 0.5 | 0.0 | 13.0 | 0.5 | 0.0 | 13.0 | 0.5 | 0.0 | 13.0 | 0.5 | 0.0 |
| | 1-Butene | 12.0 | 0.0 | 1.6 | 12.0 | 0.0 | 1.5 | 12.0 | 0.0 | 0.8 | 12.0 | 0 | 2.2 |
| | Normal Butane | 12.0 | 27.5 | 27.4 | 12.0 | 27.5 | 27.4 | 12.0 | 27.5 | 27.6 | 12.0 | 27.5 | 27.4 |
| | Cis-2-butene | 9.0 | 28.0 | 18.4 | 9.0 | 28.0 | 13.1 | 9.0 | 28.0 | 20.6 | 9.0 | 28 | 19.4 |
| | Trans-2-butene | 13.0 | 44.0 | 31.2 | 13.0 | 44.0 | 23.5 | 13.0 | 44.0 | 11.1 | 13.0 | 44 | 33.0 |
| | Butadiene | 0.0 | 0.0 | 15.0 | 0.0 | 0.0 | 26.7 | 0.0 | 0.0 | 34.2 | 0.0 | 0 | 14.0 |
| | Balance | 0.0 | 0.0 | 6.4 | 0.0 | 0.0 | 7.8 | 0.0 | 0.0 | 5.7 | 0.0 | 0 | 4.0 |
| $C_2/C_1$ | | 2.6 | — | — | 2.6 | — | — | 2.6 | — | — | 2.6 | — | — |
| First Catalyst | Catalyst A1 (Bi—Mo) (vol %) | — | — | 90 | — | — | 90 | — | — | 90 | — | — | 100 |
| Second Catalyst | Catalyst B1 (NiX) (vol %) | — | — | 10 | — | — | 0 | — | — | 0 | — | — | 0 |
| | Catalyst B2 (AgX) (vol %) | — | — | 0 | — | — | 10 | — | — | 0 | — | — | 0 |
| | Catalyst B3 (Silica-alumina) (vol %) | — | — | 0 | — | — | 0 | — | — | 10 | — | — | 0 |
| Volume of Entire Catalysts (cc) | | — | — | 17 | — | — | 17 | — | — | 17 | — | — | 17 |
| Ni Content in Entire Catalysts (g) | | — | — | 0.58 | — | — | 0.49 | — | — | 0.49 | — | — | 0.54 |
| Ag Content in Entire Catalysts (g) | | — | — | 0.00 | — | — | 0.69 | — | — | 0.00 | — | — | 0.00 |
| Butadiene Yield $R_Y$ (%) | | — | — | 21 | — | — | 37 | — | — | 48 | — | — | 19 |

INDUSTRIAL APPLICABILITY

According to the present embodiment, diene can be mass-produced in a high yield from a raw material including a branched olefin and a straight chain olefin.

The invention claimed is:

1. A method for producing diene, comprising:
   obtaining a straight chain internal olefin by removing a branched olefin from a raw material including at least the branched olefin and a straight chain olefin; and
   producing diene from the internal olefin by oxidative dehydrogenation using a dehydrogenation catalyst and an isomerization catalyst,
   wherein
   the dehydrogenation catalyst has a complex oxide including bismuth, molybdenum and oxygen, and
   the isomerization catalyst includes at least one selected from the group consisting of silica-alumina and zeolites, and
   a volume ratio between the dehydrogenation catalyst and the isomerization catalyst (volume of the dehydrogenation catalyst/volume of the isomerization catalyst) is 1.5 to 20.

2. The method for producing diene according to claim 1, wherein
   at least a part of the straight chain olefin is a terminal olefin, and
   in obtaining the straight chain internal olefin, reactive distillation is performed to remove the branched olefin from the raw material and to isomerize the terminal olefin to the internal olefin.

3. The method for producing diene according to claim 1, wherein
   the isomerization catalyst has a support and an element supported on the support,
   the support includes at least one selected from the group consisting of silica and alumina, and
   the element supported on the support is at least one selected from the group consisting of Group 10 elements of the periodic table and Group 11 elements of the periodic table, and lanthanoids.

4. The method for producing diene according to claim 3, wherein Ni is the Group 10 element of the periodic table, Cu, Ag or Au is the Group 11 element of the periodic table, and La is the lanthanoid.

5. The method for producing diene according to claim 3, wherein Ag is supported on the support as the Group 11 element of the periodic table.

6. The method for producing diene according to claim 1, wherein the isomerization catalyst includes silica and alumina, and
   a total acid amount of the isomerization catalyst measured by ammonia temperature programmed desorption is 0.11 mmol/g or less.

7. The method for producing diene according to claim 1, wherein the isomerization catalyst includes silica and alumina, and
   the isomerization catalyst has a ratio $A_2/A_1$ of 0.03 or more of an amount $A_2$ of acid sites measured in a temperature range of 600° C. or higher to an amount $A_1$ of all acid sites measured by ammonia temperature programmed desorption.

8. The method for producing diene according to claim 1, wherein
   the isomerization catalyst includes silica and alumina, and
   a molar ratio of Si to Al (Si/Al) in the second catalyst is 100 or more.

9. The method for producing diene according to claim 1, wherein
   assuming that a mass content of the branched olefin in the raw material is $C_1$ and a mass content of the straight chain olefin in the raw material is $C_2$,
   $C_2/C_1$ is 0.1 to 5.0.

10. The method for producing diene according to claim 1, wherein
    the straight chain olefin includes butene.

11. The method for producing diene according to claim 1, wherein the raw material is obtained by fluid catalytic cracking of a heavy oil fraction, and a number of carbon atoms of the branched olefin or the straight chain olefin is 4.

12. The method for producing diene according to claim 1, wherein the raw material is obtained by thermal decomposition of naphtha, and a number of carbon atoms of the branched olefin or the straight chain olefin is 4.

* * * * *